(12) United States Patent
Särelä et al.

(10) Patent No.: US 7,453,364 B2
(45) Date of Patent: Nov. 18, 2008

(54) SAFETY DEVICE SYSTEM

(75) Inventors: Antti Särelä, Espoo (FI); Marko Myllymäki, Helsinki (FI)

(73) Assignee: IST International Security Technology Oy, Helsinki (FI)

( * ) Notice: Subject to any disclaimer, the term of this patent is extended or adjusted under 35 U.S.C. 154(b) by 80 days.

(21) Appl. No.: 11/175,015

(22) Filed: Jul. 5, 2005

(65) Prior Publication Data

US 2006/0011729 A1    Jan. 19, 2006

(30) Foreign Application Priority Data

Jul. 6, 2004    (FI) .................... 20045266

(51) Int. Cl.
*G08B 23/00* (2006.01)

(52) U.S. Cl. ............ 340/573.1; 340/573.4; 340/539.11; 340/539.13; 340/545.4; 340/562

(58) Field of Classification Search .............. 340/573.1, 340/573.4, 539.11, 539.13, 545.4, 562
See application file for complete search history.

(56) References Cited

U.S. PATENT DOCUMENTS

| | | | |
|---|---|---|---|
| 4,736,196 A | 4/1988 | McMahon et al. | |
| 5,014,040 A | 5/1991 | Weaver et al. | |
| 5,515,858 A | 5/1996 | Myllymaki | |
| 5,742,233 A | 4/1998 | Hoffman et al. | |
| 5,982,285 A | 11/1999 | Bueche et al. | |
| 6,072,392 A | 6/2000 | Henderson et al. | |
| 7,064,670 B2* | 6/2006 | Galperin et al. .......... | 340/573.4 |
| 2002/0013717 A1 | 1/2002 | Ando et al. | |
| 2003/0069714 A1 | 4/2003 | Wigley et al. | |

FOREIGN PATENT DOCUMENTS

| | | |
|---|---|---|
| CH | 677 169 G A3 | 4/1991 |
| JP | 05 327595 A | 3/1994 |
| WO | WO 93/16636 | 9/1993 |

* cited by examiner

*Primary Examiner*—Tai T Nguyen
(74) *Attorney, Agent, or Firm*—Weingarten, Schurgin, Gagnebin & Lebovici LLP

(57) ABSTRACT

The invention relates to a safety device system, comprising a wearable alarm device fastenable to the wrist or elsewhere in the body or an instrument measuring physiological signals or a combination thereof, and a data terminal (6) capable of receiving messages and information from a wearable device (1). The wearable device (1) has a measurement-based identification about the device being attached to a wearer, said identification being processed for status data. The data terminal (6) has a user interface for displaying the measured status data graphically.

26 Claims, 2 Drawing Sheets

SAFETY DEVICE SYSTEM

CROSS REFERENCE TO RELATED APPLICATIONS

This application claims the benefit under 35 U.S.C. §119 (a)-(d) of Finland Patent Application No. 20045266, filed Jul. 6, 2004, the disclosure of which is incorporated by reference herein.

BACKGROUND OF THE INVENTION

1. Field of the Invention

Safety telephone is one of the commonly used emergency devices in an effort to improve safety for seniors and to promote independent living as much as possible at home, as well as in various types of nursing homes. A safety phone system comprises generally a bracelet or a necklace, provided with an alarm button. The button includes a small short-range radio transmitter for transmitting an emergency message to a base station present in the residence. The base station is connected to a telephone network and it transmits the button-sent emergency message further to a receiver. The receiver is generally an emergency exchange, which includes computer equipment for receiving alarms and messages coming from base stations over a telephone network. The alarm can also be transmitted as a voicegram or the like, for example to home attendants' mobile phones. After receiving an alarm, the receiver can place a call to the participant who has activated the alarm. The voice link can be established over the base station's speaker phone in case the participant him/herself is unable to answer the call.

2. Description of Related Art

One of the major shortcomings in available safety phone systems is that the participant is often forgetful of wearing the button, which may be a bracelet or a necklace. In a sudden emergency, for example when an elderly person falls, the alarm device is not accessible in this case. According to a British study, 27-40% of those using a safety telephone do not wear an alarm device at all or only wear it randomly [Porteus J., Brownsell S. Exploring technologies for independent living for older people, Anchor Trust, Oxon, UK, 2000, p. 60]. Thus, it can be estimated that even people in possession of a safety appliance spend in reality more than 30% of their time without the safeguard. Neither has the security service provider a possibility of monitoring use of the device, nor to make sure that clients covered by the service would indeed receive help when they need it.

Another problem results if the bracelet is used for automatic exit surveillance, for example in the case of people with dementia. In IST's Vivago system, the bracelet in possession of an elderly person, which is provided with an emergency button, functions also as an active component in exit surveillance. The bracelet transmits radio messages continuously to base stations. When a person wearing the bracelet, whose exit needs to be discovered, passes close by a base station present next to the door, the bracelet sends to the base station an identifier which is transmitted as an exit surveillance message to the receiver of alarms. It is thereby discovered that the bracelet is located in the proximity of the door. Since messages are sent by the bracelet continuously to base stations, the base station may also transmit to the receiver a disconnection message regarding the absence of bracelet-sent messages, which means that the participant has left his/her residence.

Exit surveillance is based on the supervised person wearing continuously a wirelessly communicating identifier. Thus, the receiver of alarms should also be informed in the event that the participant him/herself has removed the discussed identifier, for example unfastened the bracelet from his/her hand. If the alarm bracelet, functioning as an identifier, is not attached to the hand, exit surveillance is naturally also inoperative.

A third problem relates to wearable instruments measuring physiological signals. These include, for example, aktographs used in sleep analysis and worn around the wrist like a wristwatch, and IST's Vivago bracelet, in which aktography type measuring technology is combined with a safety alarm as described above. These instruments are used for measuring movements of the arm. In aktographs, the measurement data accumulates in the memory of a bracelet, from which it is unpacked after a test period (e.g. 2 weeks) to a PC along a cable. In the Vivago system, the measurement data is transmitted in real time wirelessly by an rf-transmitter from a bracelet to a base station, from which it can be conveyed in various ways to a measurement-data receiving PC for further analysis. The measurement data is processed in the PC for a so-called activity graph, which represents human motion activity. Generally, the activity is studied and analysed over a preceding period of several days in order to discover better for example anomalies in the participant's daily routine or quality of sleep.

If the participant disengages such a device from his/her hand, it is naturally no longer capable of measuring movements of the arm. Such occasions appear as breaks in a measuring signal, but these are impossible to distinguish from the events that the device has ceased to operate for some other reason, like as a result of the battery going flat, a technical defect or the like. If the device transmits data in a wireless manner, no data necessarily accumulates from outside the radio transmitter's range, which also appears as a break in measurement data. Having such instruments firmly attached to the hand is also important for the actual measurement. If the attachment is poor, the measuring signal shall become weaker, affecting the signal-based analysis. For these reasons, it would be highly preferential in the process of analysing measurement data to have knowledge of whether the bracelet has been attached to the hand or whether there is some other reason for the break. The problem applies generally to all wearable instruments used for measuring physiological signals. Regarding the subsequent analysis of measurement data, it is beneficial to know whether the device, and especially the sensor system, has been appropriately attached to the wearer.

The above problems can be eliminated by means of a safety device system of this invention, which has characterizing features as defined in the appended claim 1.

BRIEF DESCRIPTION OF THE SEVERAL VIEWS OF THE DRAWINGS

The invention will now be described in more detail by way of an exemplary embodiment with reference to the accompanying drawings, in which.

DETAILED DESCRIPTION OF THE INVENTION

Figure 1A:
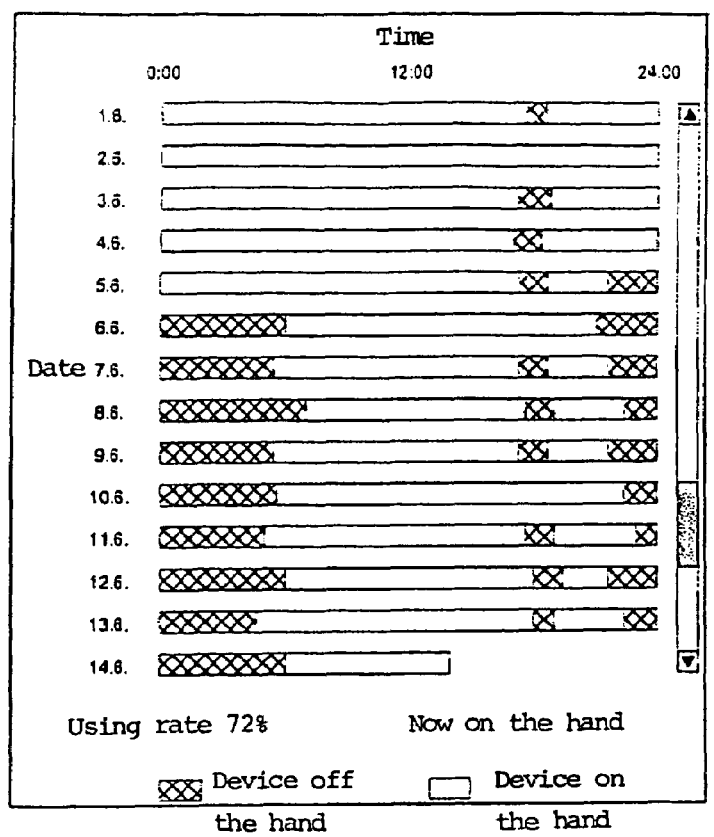
FIG. 1a is a graph of status data.

According to the invention, a wearable device 1, which can be an emergency button, an instrument measuring physiological signals or a combination thereof, includes a measurement-based automatic identifier to indicate that the participant is wearing the device. When left on a table, for example, the device records the status and transmits the data forward to a receiver of alarms or measurement data. It is part of the invention that the receiver is capable of using a data terminal 6 to detect graphically in various ways that the device is not worn by its wear. The data terminal 6 can be for example a computer, provided with a special reception program, or a mobile phone.

A measurement, based on which the device automatically identifies that it is being worn, can be performed in several ways. One method comprises a measurement of impedance, i.e. the electrical conductivity of a medium. If the device is a bracelet 1, 2, its bottom 1a can be provided with two separate contact surfaces 7, the impedance of a medium being measurable across the area therebetween. The impedance produced by the skin of a hand is about 100 kohm/cm$^2$, while air does not conduct electricity at all at discussed potentials. If between the bracelet's contacts 7 is established a direct voltage or a low-frequency alternating voltage, it is possible to infer, by measuring the electric current passing between the contacts 7, whether there is some conductive medium or air between the contacts. Based on this, it is possible to further infer whether or not the bracelet is in contact with a hand. There are several prior known ways of measuring a current. A second method is capacitive, wherein the above-mentioned contact surfaces 7 make up a capacitor which has its capacitance varying in relation to the permittivity of a medium present between the contacts 7. Respectively, it is then possible to distinguish a change of capacitance caused by a hand from having air between the contacts 7. If the device is provided with an rf-transmitter, the latter can also be used in identification. A part of the device next to the skin, such as the bottom 1a, can be designed to include a small antenna 8 for listening to the device's own rf-transmission. The device has its actual antenna 3 located as far from the skin as possible for a best possible efficiency. During the device's own rf-transmission, the bottom-fitted antenna 8 is also induced with a current whose strength depends on whether or not the bracelet is close to the skin. If the bracelet is in contact with a hand, the antenna 8 next to it connects at rf-frequencies with the hand and the induced during transmission is different from what it is when the bracelet is out of contact with a hand and the antenna 8 is surrounded by air.

Whether or not the device is in contact with a hand can also be concluded by measuring a bottom temperature of the device 1, which is also different when the device is in contact with the skin from what it is surrounded by air.

The device may also simply measure engagement data regarding, for example, in the case of a bracelet 1, 2, whether a clasp 4 is on or off.

In view of the invention, it is not essential as to which method is applied for obtaining measurement data. What is important is that the device identifies a status automatically without the participant him/herself having to consciously inform the device of the status.

According to the invention, the device informs a receiver of not being worn by the participant, the receiver processing the device-sent alarm, status or measurement data as appropriate. The information can be transmitted in real time or after a given delay through a base station 5 to the receiver's data terminal 6, such as a PC. The information can be transmitted either separately as an independent message or jointly with measurement data. In view of the invention, it is not essential as to which method is applied for informing a receiver of the device's contact status as the inventive system has a capability of using whichever appropriate method is called for. In reference to the alarm bracelet 1, 2, for example, the information can be transmitted by the bracelet's rf-transmitter to the base station 5, which is present in the residence and which relays the information by means of a modem over a public telephone network with the use of DTMF characters to the PC 6 present at an emergency exchange, from which the receiver is able to see the information.

An essential feature of the invention is that the status data can be presented graphically on the display of a receiver's data terminal 6. The graphic display can be for example a presentation as shown in FIG. 1a, consisting of vertically arranged time segments of 24 h, representing successive days, and having drawn therein a screened bar representing the time that the device has not been worn by the participant. When the bar is blank, the device is in active service. The current service status is also separately displayed on the screen, provided that the information travels in real time. The status data can also be used for working out the using rate for a given period in terms of percentage. The status data can also be scanned back in time. The figure shows that the participant has had the device off his/her hand every night since 5.6. In addition, he/she has removed the device several evenings for a couple of hours. Based on this information, the receiver can advise the user to wear the device also at nights.

Figure 1B:
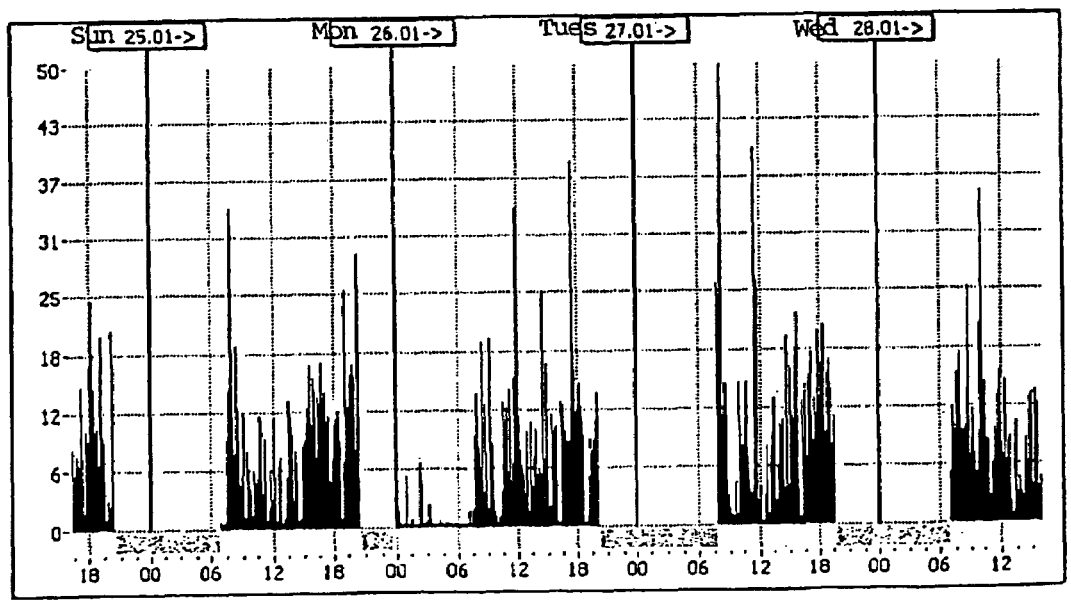
FIG. 1b is a graph of status data in combination with activity measurement. The black graph represents the participant's motion activity. The grey bar (which is coloured, e.g. yellow, on the display of a data terminal) below the graph represents time that the device has not been in contact with the hand.
Figure 2:
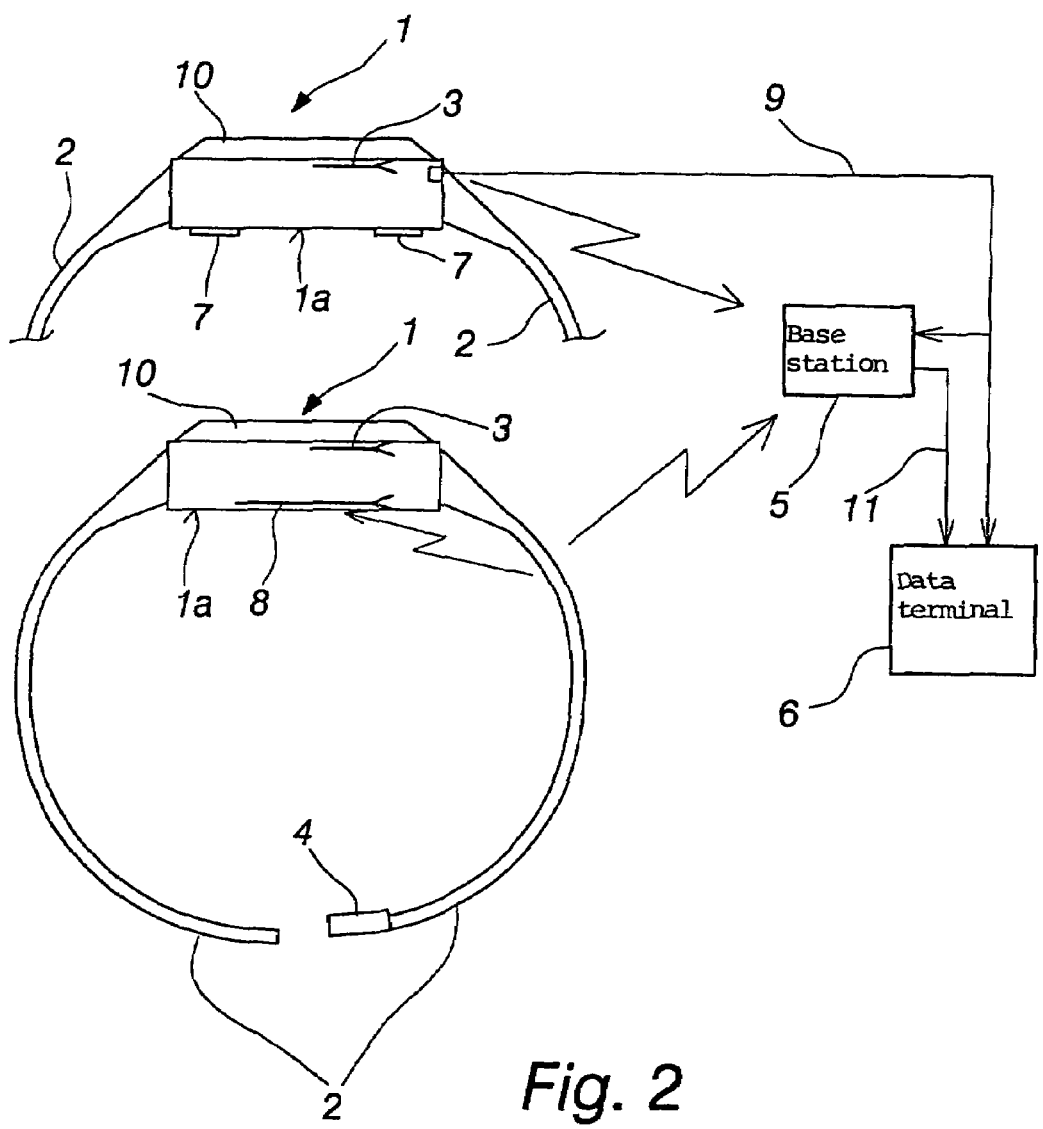
FIG. 2 shows one exemplary embodiment for the system in a block diagram.

Alternatively, the status data can be presented on a single display jointly with measurement data as shown in FIG. 1b. The depicted graph represents the participant's motion activity from the period of 4 days, wherein the graphic display has at its bottom a coloured bar to indicate points of time at which the device has not been worn. The figure shows breaks of a measuring signal in three nights and simultaneously the coloured bar (grey in the figure) indicates that the device has not been in contact with the hand. The participant habitually removes the device every evening at 19-20 o'clock. One night (26.1.), the participant has worn the device, yet in the preceding evening of 25.1. he/she has removed the device at the usual time for a couple of hours.

In view of the invention, it is not essential by which graphic method or in conjunction of which measurement data the status data will be displayed on the screen of a data terminal 6. What is essential is the receiver's ability to receive the information visually. Neither is it essential whether the displayed information comprises real-time data or historical data needed subsequently in the process of analysing the measurement data. FIGS. 1a and 1b illustrate two plausible ways of presenting status data. Just a quick glance at the graphic display is enough for the receiver to verify when the device has been active. FIGS. 1a and 1b demonstrate that the participant has not usually worn the device at night. Based on this information, the receiver may then for example advise the participant to wear the safety bracelet 1, 2 or a measuring instrument also at night for the sake of his/her safety or uninterrupted data collection.

One highly preferred application of the invention can be implemented for a combination of an emergency button 10 and an instrument 1 measuring physiological signals, such as for IST's Vivago system. This system comprises a bracelet 1, 2 provided with an emergency button 10 and a sensor measuring the participant's motion activity. The bracelet 1, 2 is provided with a sensor system 7 based on the fluctuation of capacitance for verifying whether the bracelet is on a person's hand. The bracelet includes a short-range rf-transmitter, enabling it to communicate alarms, an activity measuring signal, as well as a range of status data to a base station 5 present in the residence. The base station 5 is linked over a telephone network 11 or another communication line to a receiving PC 6. The base station 5 transmits the measurement and status data, supplied by the bracelet 1, 2, either in real time or at certain time segments to the receiver. The PC 6 is provided with a reception program, the screen of which can be used for displaying alarms, measurement and status data concerning every participant engaged in the system. The reception program can be used for a graphic display of both real-time and previously developed status data regarding use of the bracelet, jointly with a motion-activity representing graph as in FIG. 1b.

Benefits offered by the method and technology:

Receiver is able to monitor the use of safety device 1, 2 and to advice a participant to wear the device→using rate of the device rises→the participant's safety increases.

As the using rate of safety button 10 rises, the receiving organisation, such as an emergency exchange, is able to factually provide even better service, being able to guarantee a continuous safety coverage for their clients. Measurement data can be used for working out each client's using rate of the device in terms of percentage, which can be monitored and used as a code in developing the service.

If the device functions as an identifier for exit surveillance, the attending staff can immediately intervene in the event that a participant him/herself has removed the identifier. It is further possible to detect repeated occasions of a participant deactivating the device, such as night-time or the like, making it easier to anticipate such behaviour.

If the question is about a measuring instrument 1, 2, it is possible, in the process of analysing measurement data, to account for occasions in which the device has not been worn by a participant and to distinguish those occasions from other signal-breaks inducing occurrences, such as technical malfunctions. Based on this information, a person wearing the device can be advised in proper use of the device.

With the help of a graphic presentation, the receiver is able to quickly obtain essential information about using rate of the device by just a glance at the data terminal. In long-term measurements of up to several months, it is possible to browse through past data and to observe frequent occasions of the device out of service. This improves the analysis of measurement data.

The required technology is readily feasible for an existing safety phone system, which involves a wearable bracelet 1, 2 and a base station 5 apt for setting up in the residence. The implementation requires no accessories.

A sensor system 7, 8, capable of detecting whether the device is in service, is feasible for the bracelet 1, 2 by several preferred, simple and prior known procedures.

Transfer and storage of status data can be managed by using the same technology that is applied for other information coming from an alarm or measuring device.

Graphic presentation of status data is readily and preferably feasible for existing available reception programs, either as a separate display or by combining a display of status data with other display techniques.

The invention claimed is:

1. A safety device system, comprising:

a freely-removable, wearable alarm device fastenable with a fastening device to a wrist or elsewhere on a human body or an instrument measuring physiological signals or a combination thereof;

a data terminal capable of receiving messages and information from the wearable alarm device; and means for notifying the human to wear the wearable alarm device, wherein the wearable alarm device has a measurement-based identification about the wearable alarm device being attached to a wearer, said identification being processed for status data of use and non-use of the wearable alarm device, and wherein the data terminal has a user interface for displaying the measured status data of repeated periods of use and non-use graphically.

2. A system as set forth in claim 1, wherein an attachment identification for the wearable alarm device is effected by a capacitive measurement.

3. A system as set forth in claim 1, wherein an attachment identification for the wearable device is effected by measuring the impedance of a medium between contacts present in the device.

4. A system as set forth in claim 1, wherein an attachment identification for the wearable device is effected by indicating locking of a clasp present in a strap of the device.

5. A system as set forth in claim 1, wherein an attachment identification for the wearable device is effected during the transmission of an rf-transmitter present in the device by measuring a current inducing in a second antenna isolated from the transmitter.

6. A system as set forth in claim 1, wherein an attachment identification for the wearable device is effected by measuring the temperature of a part of the device which is in contact with the skin.

7. A system as set forth in claim 1, wherein the wearable alarm device is a bracelet.

8. A system as set forth in claim 1, wherein the wearable alarm device is attached by a strap to a wearer.

9. A system as set forth in claim 1, wherein the wearable alarm device transmits status data wirelessly to a base station.

10. A system as set forth in claim 1, wherein the status data can be loaded from the wearable alarm device by means of a cable coupled thereto.

11. A system as set forth in claim 1, wherein the data terminal is a computer provided with a program for receiving and displaying status data.

12. A system as set forth in claim 1, wherein the data terminal is a mobile phone provided with a program for receiving and displaying status data.

13. A system as set forth in claim 1, wherein the data terminal is a PDA device (Personal Digital Assistant) provided with a program for receiving and displaying status data.

14. A system as set forth in claim 1, wherein the data terminal's program displays status data graphically as a time segment.

15. A system as set forth in claim 1, wherein the data terminal's program displays status data graphically in conjunction with physiological measurement data.

16. A system as set forth in claim 1, wherein the data terminal's program displays status data as a variable symbol.

17. A system as set forth in claim 1, wherein the data terminal has a capability of displaying a using rate of the wearable device in percentage.

18. A system as set forth in claim 1, wherein the data terminal's program has a capability of scanning status data back in time.

19. A system as set forth in claim 1 wherein said status data includes data for anticipating a period or periods of wearable alarm device non-use or removal using automatic identifier status data of repeated instances of removal or deactivation of the wearable alarm device.

20. A system as set forth in claim 1 wherein said status data includes data for distinguishing between occasions of intentional wearable alarm device non-use or removal and other occasions of non-use.

21. A method of advising a human subject to a wear a safety alarm device, the method comprising:
   providing the human subject with the safety alarm device that includes an automatic identifier that indicates when the human subject is wearing and not wearing the safety alarm device, wherein the wearable alarm device has a measurement-based identification about the safety alarm device being attached to the human;
   monitoring the safety alarm device for automatic identifier data using a data terminal, wherein the data terminal receives messages and information from the safety device;
   determining a period or periods of non-use or removal of the safety alarm device by the human subject; and
   notifying the human subject to wear the safety alarm device.

22. A method as set forth in claim 21, wherein the data terminal monitors automatic identifier data for at least one of a change in current flow, a change in rf-transmission strength, a change in impedance, a change in capacitance, and a change in body temperature.

23. A method as set forth in claim 21, the method further comprising displaying graphical representations of automatic identifier data on the data terminal.

24. A method as set forth in claim 21, the method further comprising determining a rate of use of the safety alarm device over a period of time.

25. A method as set forth in claim 21, the method further comprising providing an emergency button on the safety alarm device.

26. A method as set forth in claim 21, the method further comprising:
   detecting periods or patterns of repeated non-use or removal of the safety alarm device using the automatic identifier data; and
   notifying the human subject to wear the safety alarm device in anticipation of said detected periods or patterns of repeated non-use or removal.

* * * * *

UNITED STATES PATENT AND TRADEMARK OFFICE
CERTIFICATE OF CORRECTION

PATENT NO. : 7,453,364 B2  Page 1 of 1
APPLICATION NO. : 11/175015
DATED : November 18, 2008
INVENTOR(S) : Antti Särelä et al.

It is certified that error appears in the above-identified patent and that said Letters Patent is hereby corrected as shown below:

Column 3, line 12, "wear" should read --user--;

Column 3, line 47, "induced during" should read --induced current during--;

Column 6, claim 4, line 25, "indicating" should read --indicated--;

Column 6, claim 5, line 28, "wearable device" should read --wearable alarm device--;

Column 6, claim 6, line 33, "wearable device" should read --wearable alarm device--;

Column 7, claim 21, line 10, "to a wear" should read --to wear--;

Column 7, claim 21, line 16, "about the safety" should read --about the--; and

Column 7, claim 21, line 20, "safety" should read --alarm--.

Signed and Sealed this

Sixteenth Day of March, 2010

David J. Kappos
*Director of the United States Patent and Trademark Office*